(12) United States Patent
Beermann et al.

(10) Patent No.: US 9,872,869 B2
(45) Date of Patent: Jan. 23, 2018

(54) USE OF NON-DIGESTIBLE SACCHARIDES FOR GIVING AN INFANT THE BEST START AFTER BIRTH

(71) Applicant: N.V. Nutricia, Zoetermeer (NL)

(72) Inventors: Christopher Beermann, Petersberg (DE); Jan Knol, Utrecht (NL); Martine Sandra Alles, Utrecht (NL); Bernd Stahl, Utrecht (DE); Günther Boehm, Leipzig (DE)

(73) Assignee: N. V. Nutricia, Zoetermeer (NL)

( * ) Notice: Subject to any disclaimer, the term of this patent is extended or adjusted under 35 U.S.C. 154(b) by 362 days.

(21) Appl. No.: 14/593,822

(22) Filed: Jan. 9, 2015

(65) Prior Publication Data

US 2015/0250807 A1  Sep. 10, 2015

Related U.S. Application Data

(63) Continuation of application No. 12/282,302, filed as application No. PCT/NL2007/050094 on Mar. 9, 2007, now abandoned.

(30) Foreign Application Priority Data

Mar. 10, 2006 (EP) .................................... 06110973
Apr. 20, 2006 (EP) .................................... 06112822

(51) Int. Cl.
| | | |
|---|---|---|
| *A61K 31/702* | (2006.01) | |
| *A23L 1/29* | (2006.01) | |
| *A23L 1/308* | (2006.01) | |
| *A23L 33/00* | (2016.01) | |
| *A23L 33/115* | (2016.01) | |
| *A23L 33/21* | (2016.01) | |

(52) U.S. Cl.
CPC .......... *A61K 31/702* (2013.01); *A23L 33/115* (2016.08); *A23L 33/21* (2016.08); *A23L 33/30* (2016.08); *A23V 2002/00* (2013.01)

(58) Field of Classification Search
CPC ... A61K 31/702; A61K 2300/00; A23L 1/308; A23L 1/293; A23V 2002/00; A23V 2200/324; A23V 2250/28; A23V 2250/1882
USPC ........................................................ 514/54
See application file for complete search history.

(56) References Cited

U.S. PATENT DOCUMENTS

| | | | |
|---|---|---|---|
| 5,032,399 A | | 7/1991 | Gorbach et al. |
| 7,858,595 B2* | | 12/2010 | Stahl .................... A61K 31/702 426/658 |
| 2004/0057943 A1* | | 3/2004 | Xaus Pey ............ A23C 9/1232 424/93.45 |
| 2004/0062758 A1 | | 4/2004 | Mayra-Makinen et al. |
| 2005/0004070 A1* | | 1/2005 | Stahl .................... A61K 31/715 514/54 |
| 2005/0015018 A1 | | 1/2005 | Dolphin et al. |
| 2006/0233772 A1 | | 10/2006 | Herz et al. |
| 2009/0305996 A1 | | 12/2009 | Beermann et al. |

FOREIGN PATENT DOCUMENTS

| | | |
|---|---|---|
| EP | 0 705 539 A2 | 4/1996 |
| EP | 1 296 694 | 4/2003 |
| EP | 1 597 978 A1 | 11/2005 |
| WO | WO 99/53777 A1 | 10/1999 |
| WO | WO 2004/112509 A2 | 12/2004 |
| WO | WO 2005/067962 A2 | 7/2005 |

OTHER PUBLICATIONS

Glossary of medical education terms, Institute of International Medical Education. http://www.iime.org/glossary.htm Accessed in Mar. 2013.*
Anderson et al. Health benefits of dietary fiber. Nutrition Reviews vol. 67(4):188-205, 2009.*
"Constipation" by BabycareAdvice.com. Retrieved on Aug. 7, 2014. Published on Sep. 20, 2004. Retrieved online at <http://www.babycareadvice.com/babycare/general_help/article.php?id=48>.
"Human Fetal Immune System Arises from Entirely Different Source Than Adult Immune System" [online]. [Retrieved on Mar. 24, 2011]. Retrieved from the internet <http://www.sciencedaily.com/releases/201 0/12/1 01216165519.htm> Published Dec. 17, 2010.
"Immune System" from KidsHealth [online Retrieved Mar. 24, 2011]. Retrieved from the internet <http://kidshealth.org/teen/your_body/bodLbasics/immune.html> Published Jun. 18, 2007.
"Immunodeficiency Disorders" from the Merck Manual Home Edition [online]. [Retrieved Mar. 18, 2011]. Retrieved from the internet <http://www.merckmanuals.com/home/printlsec16/ch184/ch184a.html>.
Anonymous, "Aptamil" [online], Jan. 16, 2004, XP002412131, http://www.milupa.ch/images/prebiotica_Pressemitteilung.pdf>, retrieved Dec. 15, 2006.
Anonymous, "Pro-Nata" [online] 2001, XP002412130, http://www.babyservice.de/beba/produkte>, retrieved Dec. 15, 2006.
Definition of "prevention" from the Institute for International Medical Education [online], [Retrieved on Mar. 24, 2011]. Retrieved from the internet <http://www.iime.org/glossary.htm>. Published Feb. 2002, p. 1, 2, 26, 27 and 39.
Gibson, et al. "Trans-Galactooligosaccharides as Prebiotics", *Handbook of Functional Diary Products*, published by CRC Press, 2003, pp. 91-108.
Kalliomaki, et al, "Probiotics in Primary Prevention of Atopic Disease: A Randomised Placebo-Controlled Trial," *The Lancet*, Lancet Limited, London, GB, vol. 357, No. 9262, Apr. 7, 2001, XP005061313, pp. 1076-1079, abstract.

(Continued)

*Primary Examiner* — Yih-Horng Shiao
(74) *Attorney, Agent, or Firm* — Gilberto M. Villacorta; Sunit Talapatra; Foley & Lardner LLP

(57) ABSTRACT

A food or supplement for pregnant women comprising water soluble, non-digestible saccharides is described. The composition is used to improve the flora and/or immune system of the pregnant women, to improve the immune system of the infant and to improve the intestinal flora of the infant after birth.

6 Claims, No Drawings

(56) References Cited

OTHER PUBLICATIONS

Kolida, et al. "Prebiotic effects of insulin and oligofructose", *British Journal of Nutrition*, 2002, Supplemental, vol. 87, No. 2, pp. S193-S197.

Loo, "Prebiotics Promote Good Health", *J Clin Gastorenterol*, Jul. 2004, vol. 38, Supp. 2, pp. S70-S75.

Mold, J.E., Venkatasubrahmanyam, S., Burt, T.D., Michaelsson, J., Rivera, J.M., Galkina, SA, Weinberg, K., Stoddart, C.A., McCune, J.M., "Fetal and Adult Hematopoietic Stem Cells Give Rise to Distinct T Cell Lineages in Humans" *Science*, 2010, vol. 330, pp. 1695-1699.

Tomasik, P.J., Tomasik, P., (2003) Probiotics and Prebiotics. *Cereal Chemistry*, vol. 80, No. 2, pp. 113-117.

\* cited by examiner

USE OF NON-DIGESTIBLE SACCHARIDES FOR GIVING AN INFANT THE BEST START AFTER BIRTH

CROSS-REFERENCE TO RELATED APPLICATIONS

This application is a Continuation of U.S. application Ser. No. 12/282,302, which is a U.S. National Stage of PCT/NL2007/050094, filed Mar. 9, 2007, and claims priority of European Patent Application Nos. 06110973.2 and 06112822.9, filed Mar. 10, 2006 and Apr. 20, 2006, respectively. The disclosures of these prior-filed applications are incorporated by reference herein in their entirety.

FIELD OF THE INVENTION

The present invention relates to a composition for stimulating health of an infant by administering the composition to a pregnant woman.

BACKGROUND OF THE INVENTION

For the mother it is particularly important that the baby develops well during pregnancy and gets an optimal start when it is born. Hence, pregnant women often ingest nutritional compositions which aim to improve growth and development of the unborn child.

Long chain poly-unsaturated fatty acids (LC-PUFA) have been described to stimulate the brain development of the unborn child. For that reason, pregnant (and lactating) women ingest nutritional compositions with LC-PUFA. EP705539 describes such a composition.

EP1296694 relates to prophylaxis of allergies, and relates specifically to primary prevention of atopic diseases by administering probiotic bacteria, beneficial microbes present in a healthy gut flora, pre- and postnatal to children at high risk of atopic diseases.

SUMMARY OF THE INVENTION

The inventors have found that administration of a water-soluble, non-digestible saccharide to pregnant women improves the immune system of the unborn infant. It was round that the unborn child has an enhanced expression of the receptors CD14, and TLR 2 as present in the membrane of enterocytes and monocytes.

Additionally, it was found that the development of the intestinal flora of the infant delivered by a mother who has ingested the present saccharide is improved compared to the development of the intestinal flora of an infant delivered by a mother that did not ingest the present saccharide.

The inventors have found that the intestinal flora development of the infant is improved as a result of an improved intestinal and/or vaginal flora of the mother ingesting the present saccharide. After ingestion of the present saccharides, the growth of bifidobacteria and lactobacilli in the gastrointestinal tract of the mother is stimulated. Subsequently, by cross colonisation, the vaginal flora of the mother is also beneficially changed towards a high content and diversity of the bifidobacteria and lactobacilli. During birth, the neonatal gut is first inoculated by maternal vaginal and intestinal microflora. Hence, an advantageous vaginal and intestinal flora of the mother results in an improved flora of the infant in the first period of life.

As a result of the stimulated immune system and optimal intestinal flora dominated by the genera *Bifidobacterium* and *Lactobacillus* the infant has reduced chances to develop immune related disorders, such as atopic diseases, but also gastro-intestinal disorders, such as infections, intestinal inflammation, diarrhoea or constipation.

In a further aspect it was surprisingly found that administration of this non-digestible saccharide beneficially affected the immune system of the pregnant women and/or of the infants. It was found that the child immune system before delivery is primed towards a faster Th1 response after birth. As a result the chances to develop immune related disorders, such as atopic diseases, is even further reduced.

DETAILED DESCRIPTION OF THE PREFERRED EMBODIMENTS

The present invention provides the use of a water soluble, non-digestible saccharide for the manufacture of a composition for
  i) improving the intestinal flora development of an infant after birth;
  ii) strengthening the immune system of an infant before birth; and/or;
  iii) strengthening the immune system and/or prevention of immune system related disorders of the infant after birth;
wherein the composition is administered to a woman pregnant of said infant.

The present invention further provides the use of water soluble, non-digestible saccharide for the manufacture of a composition for
  i) strengthening the immune system of a pregnant woman;
  ii) improving the intestinal flora of a pregnant woman; and/or
  iii) improving the vaginal flora of a pregnant woman;
wherein the composition is administered to the pregnant woman.

Water Soluble, Non-Digestible Saccharide

The composition used in the present method comprises water soluble, non-digestible saccharides. The term "non-digestible" as used in the present invention refers to saccharides which are not digested in the intestine by the action of acids or digestive enzymes present in the human upper digestive tract (small intestine and stomach), but which are fermented by the human intestinal flora. Mono- and disaccharides such as glucose, galactose, fructose, sucrose and lactose are digestible. The term "fermentable" as used herein refers to the capability to undergo conversion by microorganisms in the lower part of the gastro-intestinal tract (e.g. colon) to smaller molecules, in particular short chain fatty acids and lactate. The present saccharide is water-soluble, which can be determined with the method described by L. Prosky et al, J. Assoc. Anal. Chem 71: 1017-1023, 1988.

The present saccharides preferably have a degree of polymerisation (DP) of at least 2 and preferably below 100 monosaccharide units, preferably below 60, even more preferably below 40, most preferably below 10. Preferably, the present water soluble, non-digestible saccharide is a galactose comprising saccharide. A saccharide with a relatively low degree of polymerisation has an improved fermentability by lactobacilli and/or bifidobacteria and further does not have the technological disadvantage to increase the viscosity.

Water Soluble, Non-Digestible Galactose Comprising Saccharide

The present saccharide is preferably a water soluble, non-digestible galactose containing saccharide (hereinafter referred to as "GAL-oligo"), which preferably comprise at least 50% galactose units based on the total number of monosaccharide units of the saccharide. GAL-oligo has an improved bifidogenic effect compared to other water soluble, non-digestible saccharides. Human breast milk also comprises a high concentration of GAL-oligo and infants fed human breast milk have an intestinal flora more rich in bifidobacteria than infants fed a standard infant milk formula. Preferably the present GAL-oligo contains at least 60% galactose units based on the total number of monosaccharide units present in the saccharide, more preferably, at least 65%.

The present GAL-oligo preferably comprises at least two terminal saccharide units, wherein at least one terminal saccharide unit is selected from the group consisting of glucose and galactose; and at least one terminal saccharide unit is selected from the group consisting of galactose and fucose. Preferably at least 75% of the saccharides of the GAL-oligo are β-linked, preferably 100%.

The term "terminal saccharide" refers to a saccharide which is bound to one other saccharide unit (e.g. galactose, glucose, fructose or fucose). The present GAL-oligo preferably contains not more than 4 terminal saccharides, preferably not more than 2. In a preferred embodiment, the GAL-oligo comprises at least one terminal galactose and one selected from at least terminal glucose and one terminal fucose. Even more preferably, the present GAL-oligo comprises at least one terminal galactose and at least one terminal glucose. Preferably the present Gal-oligo contains 2 terminal saccharide units and has a degree of polymerisation (DP) of 2 to 60.

Preferably the GAL-oligo is selected from the group consisting of transgalactooligosaccharides, galactooligosaccharides, lacto-N-tetraose (LNT), lacto-N-neotetraose (neo-LNT), fucosyl-lactose, fucosylated LNT and fucosylated neo-LNT. Preferably the GAL-oligo is sialylated. Preferably the GAL-oligo is selected from the group consisting of sialyllactose, sialylfucosyllactose, sialyllactosamine and sialyl-LNT and sialyl-neo-LNT, more preferably sialyllactose. In a particularly preferred embodiment the present method comprises the administration of transgalactooligosaccharides ([galactose]$_n$-glucose; wherein n is an integer between 1 and 60, i.e. 2, 3, 4, 5, 6, ..., 59, 60; preferably n is selected from 2, 3, 4, 5, 6, 7, 8, 9, or 10). Preferably the saccharides of the transgalactooligosaccharides are β-linked. Transgalactooligosaccharides (TOS) are for example present in a composition sold under the trademark Vivinal™ (Borculo Domo Ingredients, Netherlands). Other suitable sources of TOS are Cup-oligo and Bi²muno.

Different Water Soluble, Non-Digestible Saccharides

In order to achieve an even better effect regarding intestinal flora and/or (improvement of) the immune system of the infant or of the intestinal flora, vaginal flora and/or (improvement of) the immune system of the pregnant woman, the present composition preferably comprises IWO different water soluble, non-digestible saccharides, differing from each other in structure. Each water soluble, non-digestible saccharide is fermented by different species of micro-organisms in the intestinal and/or vaginal flora and/or on a different location in the intestinal tract, resulting in an improved flora and greater diversity of bacteria.

The present invention provides a composition which preferably comprises water soluble, non-digestible saccharide A and water soluble, non-digestible saccharide B. Saccharide A and saccharide B have different glycosidic linkages, a different degree of polymerisation and/or a different monosaccharide composition. Preferably, saccharide A is a GAL-oligo.

According to a preferred embodiment of the present invention, the percentage of at least one monosaccharide unit selected from the group consisting of glucose, fructose and galactose in saccharide A is at least 40% higher than the percentage of the same monosaccharide unit in saccharide B, preferably at least 50%, more preferably at least 75%, even more preferably at least 90%. An increased diversity of monosaccharide units stimulates a wider population of intestinal (beneficial) bacteria, resulting in an improved flora. The percentage of a monosaccharide unit in the saccharide can be simply calculated by dividing the number of the respective monosaccharide units (e.g. glucose) present in the saccharide by the total number of the monosaccharide units present in that saccharide.

Preferably water soluble, non-digestible saccharide A and B have a degree of polymerisation (DP) between 2 and 200. Preferably at least 80 wt. %, more preferably at least 95 wt. %, most preferably at least 98 wt. % of the cumulative weight of water soluble, non-digestible saccharide A and B has a degree of polymerisation (DP) below 100, more preferably below 60, most preferably below 40. The lower DP advantageously reduces viscosity and increases fermentability of the non-digestible saccharides. Preferably, at least 50 wt. %, more preferably at least 75 wt. % of the cumulative weight of water soluble, non-digestible saccharides A and B has a DP of 2 to 8. By using a mixture with a high weight percentage of saccharides with a low DP the fermentability and stimulatory effect on the growth of the lactic acid bacteria and bifidobacteria will be increased.

According to a preferred embodiment of the present invention, the DP of water soluble, non-digestible saccharide A is at least 5 monosaccharide units lower than the DP of water soluble, non-digestible saccharide B, preferably at least 10, even more preferably at least 15. Including a saccharide with an increased degree of polymerisation reduces the osmotic load, and results in a prolonged fermentation along the colon, thereby improving stimulation of beneficial bacteria also in more distal parts of the colon. Preferably, water soluble, non-digestible saccharide A has a DP of 2-10, more preferably 2-8. Preferably the water soluble, non-digestible saccharide B has DP of 11-100. The water soluble, non-digestible saccharides A and B with a different DP may have the same or slightly different monosaccharide composition, preferably different monosaccharide compositions.

In a preferred embodiment of the present invention the percentage of at least one glycosidic linkage of water soluble, non-digestible saccharide A based on total glycosidic linkages of present in saccharide A is at least 40% higher than the percentage of the same glycosidic linkage in water soluble, non-digestible saccharide B, preferably at least 50%, even more preferably at least 75%. The term "glycosidic linkage" as used in the present invention refers to a C—O—C bond formed between the rings of two cyclic monosaccharide units by the elimination of water. An increased diversity in glycosidic linkages stimulates a wider range of beneficial bacteria. Glycosidic linkages differ in that they covalently bind carbon atoms in the monosaccharide units at differently numbered positions, and/or that they form α or β bonds. Examples of different glycosidic linkages occurring in water soluble, non-digestible saccharides are β(1,3), α(1,4), β(2,1), α(1,2), and β(1,4) linkages. Preferably the glycosidic linkages in water soluble, non-digestible saccharide A comprises at least 40% β(1,4) glycosidic linkages, more preferably at least 75%. The glycosidic linkages in water soluble, non-digestible saccharide B preferably comprise at least 40% β(2,1) glycosidic linkages, more preferably at least 75%.

In a preferred embodiment the present composition contain a combination of Gal-oligo and a water soluble, non-digestible saccharide selected from the group consisting of fructopolysaccharides (such as inulin), more preferably a combination of GAL-oligo Which have an average DP between 2 and 10 and a water soluble, non-digestible saccharide selected from the group consisting of fructopolysaccharides and fructooligosaccharides, most preferably a combination of transgalactooligosaccharides and inulin.

Preferably saccharide A and saccharide B are in a weight ratio of 3/97 to 97/3, more preferably 5/95 to 95/5. Having both saccharide A and B present in a sufficient relative proportion will have a better effect on flora. Most preferably the weight ratio of saccharide A to B is 2/3 to 95/5. A slight excess of saccharide A, being preferably a GAL-oligo and/or an oligosaccharide, is even further preferred as this will have a better effect on the flora.

Long Chain Polyunsaturated Fatty Acids (LC-PUFA)

Preferably, the present composition additionally comprises long chain polyunsaturated fatty acids and/or long chain polyunsaturated fatty acyl chains (LC-PUFA). The term LC-PUFA in the present invention relates to a fatty acid or fatty acyl chain with a length of 20 carbons or more and at least two unsaturated bonds. Preferably, the composition comprises a LC-PUFA selected from the group consisting of eicosapentaenoic acids and/or acyl chain (EPA), docosahexaenoic acid and/or acyl chain (DHA) and arachidonic acid and/or acyl chain (AA). In one embodiment the composition comprises DHA. In another embodiment the composition comprises AA. More preferably the composition comprises DHA and AA. LC-PUFA advantageously strengthen the immune system of the infant to be horn. Hence, administration of a composition comprising both a water soluble, non-digestible oligosaccharide and LC-PUFA to a pregnant women will have an improved effect in the immune system of the infant compared to the Water soluble, non-digestible saccharide alone.

The weight ratio EPA/DHA is preferably 1 or lower, more preferably below 0.5. The LC-PUFA may be provided as free fatty acids, in triglyceride form, in phospholipid form, or as a mixture of one of more of the above. The present composition preferably comprises at least one of AA and DHA in phospholipid form. Preferably the weight ratio DHA to AA is between 0.1 and 20, more preferably between 0.5 and 5.

Preferably the composition comprises 50 to 3000 mg LC-PUFA per daily dose, more preferably 100 to 1500 mg, most preferably 200 to 500 mg.

Other Components

In a preferred embodiment the composition additionally comprises probiotics. Probiotics in the present invention refer to micro-organisms, which upon administration exert a beneficial effect on the host. Probiotics have beneficial effects on intestinal flora, vaginal flora and/or the immune system of pregnant women and their infant to be born, hence the combination of a water soluble, non-digestible saccharide and probiotics will have a superior effect on intestinal flora and/or immune system of both. Preferably, the probiotics are selected from the group consisting of *Lactobacillus* and *Bifidobacterium*. More preferably, the probiotic is selected from the group consisting of the *Lactobacillus accidophilus* group, *L. rhamnosus, L. casei, L. paracasei, L. plantarum, L. reuteri, L. fermentum, Bifidobacterium infantis, B. animalis* subsp. *lactis, B. breve, B. longum*, and *B. bifidum*. Even more preferably, the probiotics are *L. paracasei* and/or *B. breve*, since administration of water soluble, non-digestible saccharide stimulates most species of *Lactobacillus* and *Bifidobacterium* population to an equal extent, but stimulates *B. breve* and *L. paracasei* to a lesser extent. Since bifidobacteria are more dominant in the infant intestinal flora than lactobacilli, *B. breve* is preferred most. Preferably, probiotics are present in a daily dose of $1\times10^6$ colony forming units (cfu) to $1\times10^{13}$ cfu, more preferably $1\times10^7$ to $1\times10^{11}$ most preferably $1\times10^8$ to $1\times10^{10}$ of each different probiotic.

The composition comprises additionally vitamins and minerals beneficial for pregnant women. Often, supplements comprising vitamins and minerals are ingested by pregnant women for their or the foetus' benefit. Inclusion of these vitamins and minerals in the present composition conveniently reduces the amount of compositions to be taken by pregnant women. Preferably, the composition comprises at least one component, more preferably at least three components, most preferably at least six components selected from the group consisting of folic acid, vitamin B1, vitamin B2, vitamin B6, vitamin A, vitamin D, iron, zinc, and iodine. Preferably, these components are present in a daily dose of 25 to 100% of the recommended daily allowance (RDA), more preferably between 45 to 100%. Preferably vitamin A is supplied as β-carotene.

The Composition

The composition comprising the water soluble, non-digestible saccharide may be administered to the pregnant women in the form of a bar, a capsule, a tablet, a liquid, or a powder.

Preferably, the composition is a milk-based liquid, comprising fats, proteins and digestible carbohydrates. Preferably the fat content of the milk-based liquid is less than 2 g/l in order to keep the amount of calories to be consumed low. Preferably this milk-based liquid is packed into a bottle or tetrapack with a volume of 50 to 1000 ml, more preferably 60 to 500, most preferably 75 to 125 ml. Preferably, the composition is a bar, i.e. a solid, chewable composition with a water activity below 0.8, preferably below 0.65. Preferably, the composition is a powder, packed in sachet comprising 1 to 10 g, more preferably 1.5 to 7 g, most preferably 2 to 5 g.

Dose

In the present method, preferably the present saccharide is administered to the pregnant women in an amount between 0.5 and 50 g per day, preferably between 3 and 25 g per day, most preferably between 6 and 12 g per day. Preferably, this daily dose is administered in one portion per day. Preferably, this daily dose is divided over 2 or 3 or 4 portions, which are consumed 2, 3 or 4 times per day, respectively.

Preferably, the composition is administered to the pregnant women at least 2 weeks before due delivery, more preferably at least 6 weeks, most preferably at least 12 weeks.

Applications

Depending on the jurisdiction it is to be understood that in the part hereinbelow where a method of a certain treatment is mentioned, said method comprising administering an effective amount of a composition as described hereinabove or administering an effective amount of at least a water soluble, non-digestible saccharide to a pregnant woman, this also relates to the use of a at least a water soluble, non-digestible saccharide for the preparation of a composition for said purpose. Both manners of putting the present invention to words is also covered by the wording such as the present composition is used for a certain purpose or the administration of the present composition is used for a certain purpose.

A method for improving the intestinal flora and/or the immune system of an infant is provided, said method comprising administering the composition of the present invention, i.e. a composition comprising water soluble, non digestible saccharides, to a woman pregnant of said infant.

In one embodiment the immune system of the infant is strengthened. Strengthening the immune system in the present invention relates to improvement, stimulation and/or enhancement of the immune system. Preferably the improvement, stimulation and/or enhancement is with respect to a control group, which in the context of this invention means with respect to a pregnant woman that did not ingest water soluble, non-digestible saccharide. The inventors observed that administration of a water soluble, non-digestible saccharide directed the neonatal immune system towards a Th1 response and/or improved the Th1/Th2 balance. It was found that before delivery the immune system of the unborn child is primed by enhancing the receptors CD14 and TLR 2.

In one embodiment, administration of water soluble, non-digestible saccharide to pregnant women is used for preventing the onset of atopic diseases in the infant. In one embodiment the composition is administered to pregnant women in order to prevent the incidence and/or reduce the severity of allergy (i.e. food allergy), eczema (i.e. atopic dermatitis), asthma, rhinitis, hayfever, rhinoconjunctivitis, and/or wheezing in the infant, most preferably allergy and/or atopic dermatitis. Eczema, i.e. atopic dermatitis, is characterized by a dry and/or red and/or an itchy skin.

In one embodiment administration of the water-soluble, non-digestible saccharide to in the pregnant women, is used to improve the intestinal flora of the infant. Administration of the present composition is in an embodiment used for enhancing the percentage bifidobacteria and/or lactobacilli in the colon and/or faeces based on total bacteria present in the flora and/or faeces of the infant after birth. A flora rich in bifidobacteria and/or lactobacilli strengthens the immune system of the infant and improves the gastro-intestinal health. An improved gastro-intestinal health relates to a reduced incidence of gastro-intestinal infections, a shorter duration of intestinal infections, a reduced incidence and severity of gastro-intestinal inflammation, a reduced incidence and/or severity of diarrhoea, reduced constipation, or reduced cramps compared to the gastro-intestinal health of an infant of which the mother during pregnancy did not ingest the present composition comprising water-soluble, non-digestible saccharide. Strengthening or strengthened and improving or improved in the context of this invention is relative to an infant of which the mother during pregnancy did not ingest the present composition comprising water-soluble, non-digestible saccharide or relative to a pregnant woman that did not ingest the present composition comprising water-soluble, non-digestible saccharide. A strengthened immune system will have a preventive effect on atopic diseases and/or respiratory infections. In one embodiment administration of the present composition to a pregnant woman is used to prevent and/or reduce the severity of disorders selected from the group consisting of allergy (i.e. food allergy), eczema (i.e atopic dermatitis), asthma, rhinitis, hayfever, rhinoconjunctivitis, wheezing, intestinal infections, vaginal infections, respiratory infections, diarrhoea, constipation, cramps and intestinal inflammation in the infant after birth. In one embodiment administration of the present composition to a pregnant woman is used to prevent disorders selected from the group consisting of intestinal infections, respiratory infections, diarrhoea, constipation, cramps and/or intestinal inflammation of the infant after birth.

Packages comprising the present composition according to the invention with a text stating that upon consumption of the composition a pregnant woman will give her child the best start after birth, for example regarding intestinal colonisation, intestinal flora, flora composition and/or immune system, e.g. immunological defense or strengthened or improved or enhanced or stimulated immunity are also encompassed.

Administration of the composition of the invention is in one embodiment used to improve the immune system of the pregnant women.

Administration of the composition of the present invention, comprising water soluble, non-digestible saccharides, preferably comprising two different water soluble, non-digestible saccharides, is in one embodiment used to strengthen the immune system, the intestinal flora and/or the vaginal flora of a pregnant woman. In an advantageous embodiment administration of the present composition, preferably comprising two different water soluble, non-digestible saccharides, is used to enhance the percentage of lactobacilli and/or bifidobacteria based on total bacteria present in the intestine and/or vagina of the pregnant women. This is of importance since a disturbed vaginal flora is frequently found during pregnancy and the overgrowth of pathogens and breakdown of the vaginal microbial microenvironment can be prevented by a stable colonization with lactobacilli.

EXAMPLES

Example 1 Clinical Trial

CA prospective, double-blind, randomized, placebo controlled study with a parallel group design was performed with a total of 33 pregnant healthy volunteers. They received either the experimental supplement or a placebo from the 25th week of gestation until delivery. The experimental supplement was based on non-digestible oligosaccharides, and comprised 3 g of GOS (from Vivinal GOS, Borculo Domo, The Netherlands) plus inulin (RaftilinHP, Orafti, Belgium), in a 9:1 wt/wt ratio and 3 g of digestible maltodextrin. This supplement was taken 3 times a day. The control supplement was composed of 6 g digestible maltodextrin.

A stool sample was taken before the first supplementation, at the 25th week of gestation. A second stool sample was taken at the last standardized routine hospital visit before delivery. At delivery, one cord blood sample was obtained from the placental umbilical vein. At day 5, day 20 and 6 month after delivery stool samples were obtained from the neonates.

Microbial flora of the maternal and neonatal stool samples were analysed by FISH and real time PCR. Cord blood (CB) was phenotypically characterized using FACS analysis and in vitro stimulation assays with mitogens and allergens.

The following parameters were measured using methods known in the art:
a) Innate Immune Response NKT cells, frequency of monoclonal T cell receptors (i.e. homogeneous N-region of Va24JaQ TCR, quantification of Toll-like receptor expressing cells (TLR2, TLR4); granulocytes count. NK-cell activity b) Adaptive Immune Response Lymphocyte subsets were by four-color-cytometry. Characterization of the TH1/TH2-related mRNA cytokine and chemokine receptor patterns (TNF-a, INF-g, IL-4, IL-8, IL10, IL-12, IL-13, TGFβ, CD25, CD45RA, CD45RO, CTLA-4, CCR3, CCR4, CCR5, CXCR3) in non-stimulated cells were determined by Real-time RT PCR and after whole blood stimulation with ConA/PHA and LPS ex vivo. Analysis of the ratio of TH1/TH2-cytokine production within $CD4^+$ and $CD8^+$T-cell subsets were determined.

Placental cortical blood samples were obtained form 28 deliveries and stimulated with ConcanavalinA (ConA)/(PHA), Lipopolysaccharide (LPS), *Staphylococcus* enterotoxin B (SEB), β-lactoglobulin (BLG), major house dust mite allergen from *Dermatophagoides pteronyssinus* (Der p1), ovalbumin (Ova), for 24 h.

CB T lymphocytes (50 μL whole blood samples) were stained with appropriately diluted FITC-, PE-, PC5-, or APC-labeled monoclonal antibodies against human CD4, CD8, CD45RA, CD45RO, CD25, CD69, CCR4, CCR5, CD14, CCR1, CCR2, CCR6, CCR7, CCR8, CCR9, CXCR3, CXCR4, CXCR5, CRTH2, and appropriate isotype controls. After staining, contaminating erythrocytes were lysed. The percentages of chemokine receptor ($CKR^+$) and of $CKR^+CD45RA^+$ expressing lymphocytes within the $CD4^+$ T helper (Th) population, and the percentages of $CKR^+$ expressing cells within the $CD4^+D45RA^+$ population were analyzed. The same analyses procedure was performed within the $CD8^+$ T cytotoxic (Tc) and $CD8^+CD45RA^+$ lymphocyte populations. For CXCR4 the mean fluorescence intensity (MFI) was determined. $CD4^+CD25^{high}$ expression on T regulatory cells was determined.

Whole CB Stimulation Assay

Heparinized CB was diluted 1 to 5 in RPMI-1640. Aliquots of 1 mL diluted CB were stimulated with concavalin A (Con A 50 μg/mL), beta-lactoglobulin (100 μg/mL BLG), ovalbumin (100 μg/mL OVA), lipopolysaccharid (0.1 μg/mL LPS), staphylococcal enterotoxin B (0.1 μg/mL SEB), *Dermatophagoides pteronyssinus* (10 μg/mL Der p1) or medium alone in a 24-well culture plate. Cells were incubated at 37° C. in a 5% $CO_2$-atmosphere for 24 h or 48 h and supernatants were stored at −80° C. for cytokine analyses.

Multiplex Array

The cytokines were quantified in culture supernatants with a human multiplex, particle-based, flow cytometric assay. TNF-α, IFN-γ, IL-1β, IL-2, IL-4, IL-10, GM-CSF, G-CSF concentrations in the supernatants were directly measured without further dilution. To determine IL-6, IL-8, MCP-1 and MIP-1β supernatants were diluted 1:10 in RPMI. The differences in cytokine expression, as compared to the negative control, were determined and concentrations were normalized to the number of lymphocytes (for IL-2) and total leukocytes (for all other cytokines) obtained from whole blood count (pg/ml/10E3 cells).

Despite large intra-individual variations in the maternal microflora composition, the total bacterial load and the median numbers of cells/ml of bifidobacteria and Lactobacilli did not differ between both groups before onset of supplementation. However, upon supplementation with the supplement comprising GOS and inulin an increased percentage of total bifidobacteria and lactobacilli in the faecal flora of the pregnant woman was observed. See Table 1. In maternal stool samples, *B. catenulatum, B. infantis* and *L. acidophilus* were the most frequent species in both groups before and after supplementation.

The faeces of the infants from mothers from the experimental group contained, at day 5 after delivery, 7.4% lactobacilli (n=17, s.e. 3.0), whereas the faeces of infants of mothers of the control group, at day 5 after delivery, contained only 2.4% lactobacilli (n=16, s.e. 0.9).

Intra-group comparisons of infants showed a significant increase in the numbers of lactobacilli in the placebo group [p=0.038; pW] from day 20 to day 182. This effect was confirmed by FISH analyses [p=0.018; pW]. The percentage of neonates positive for *L. acidophilus* increased in the placebo group from day 20 to day 182 [p=0.016]. This difference was confirmed by qPCR (analyses (p=0.012).

FACS analysis of cord blood revealed significantly lower mean fluorescence intensity levels of $TLR^{2+}$ on $CD14^+$ monocytes in the experimental group (p<0.05). The altered CD14+ and TLR2+ expression levels indicate that the neonatal immune system before delivery is directed towards a faster Th1 response after delivery.

TABLE 1

Percentage bifdidobacteria and lactobacilli in faeces of pregnant women consuming a mixture of GOS and inulin (experimental) or maltodextrin (control).

| | Experimental Mean (s.e.) % bifido-bacteria[a] | Experimental Mean (s.e.) % lactobacilli[a] | Control Mean (s.e.) % bifido-bacteria[a] | Control Mean (s.e.) % lactobacilli[a] |
|---|---|---|---|---|
| T = 1[b] | 13.0 (1.7)[c] | 8.6 (2.0) | 18.5 (4.1) | 5.4 (1.9) |
| T = 2[b] | 24.1 (2.6)[cd] | 9.9 (1.7) | 14.7 (3.5)[d] | 7.8 (1.9) |

[a] Bifidobacteria were quantified with FISH, lactobacilli were quantified by real time PCR.
[b] t = 1 in 25th week of gestation, before onset of supplementation, t = 2 is at the last hospital visit before delivery.
[c] Statistically significant difference, p < 0.05, between t = 1 and t = 2
[d] Statistically significant difference, p < 0.05, between experimental and control group.

To test if maternal prebiotic supplementation affected fetal immunity, a comprehensive phenotypical lymphocyte subset analyses was performed. CB $CD4^+$ T helper (Th) cells and $CD8^+$ T cytotoxic (Tc) cells predominantly expressed the naïve ($CD45RA^+$) phenotype (>84%) while less than 13% expressed $CD45RO^+$. The ratio of $CD4^+/CD8^+$ as well as the percentages of $CD4^+CD45RA^+$, $CD8^+CD45RA^+$, $CD4^+CD45RO^+$ and $CD4^+CD45RO^+$ did not differ significantly between the prebiotic and the placebo groups. In contrast to the high frequency of $CCR7^+$ (>87.3%) cells, all other CKRs were expressed at a very low frequency on both $CD4^+$ and $CD8^+$ cells. The MFI of CXCR4 was high on both $CD4^+$ and $CD8^+$ subsets, while CXCR3 was only expressed at a high frequency on $CD8^+$ cells. The analyses of the frequency of $CKR^+$ lymphocytes within $CD4^+$, $CD8^+$, $CD4^+CD45RA^+$ and $CD8^+CD45RA^+$ CB T cell subsets, as well as the Th1/Th2 ratio (CXCR3/CCR4 and CCR5/CCR4) within the different $CD4^+$ and $CD8^+$ subsets, did not differ significantly between the two to groups. The early activation marker CD69 as well as the late activation marker CD25 were expressed at similar levels on the different $CD4^+$ subsets in both groups (data not shown). No difference in the frequency of $CD25^{high}$ expressing $CD4^+$ T cell subsets was observed (median: 1.5 versus 1.4; p=0.683).

The comparative analyses of leukocyte-derived cytokine profile production by whole CB cultures stimulated with mitogen and allergens for 24 h revealed typical patterns of cytokine expression. No significant differences between the two supplementation groups were observed, when analyzing the cytokine concentrations induced by different stimuli (apart from G-CSF (p<0.03 for Der p1, BLG and OVA).

These results indicate that supplementation with water soluble non-digestible saccharides resulted in increased percentage of bifidobacteria and lactobacilli in the gut microflora of pregnant women. This results in an improved inoculation of the intestine of the infant during birth and colonisation after birth with lactobacilli and/or bifidobacteria. Especially the presence of lactobacilli very soon after birth is of importance, since lactobacilli have a high capacity of acidification of the colon, thereby making the intestinal environment subsequently more suitable for bifidobacteria and less suitable for enteral pathogens. Furthermore, these results indicate that this supplementation improves the immune system of the unborn child and infant during and after birth.

Example 2

100 ml of a liquid milk-based composition packed in a 100 ml bottle comprising:
- 8.1 g transgalacto-oligosaccharide, (originating from Vivinal GOS)
- 0.9 g fructopolysaccharide (originating from RaftilineHP)
- 750 mg fish oil and evening primrose oil, comprising
  - 300 mg DHA
  - 42 mg EPA
  - 8.4 mg AA
  - 8.4 mg docosapentaenoic acid (DPA)
  - 15 mg gamma linoleic acid (GLA)

The invention claimed is:

1. A method of improving the intestinal microflora development of an infant after birth; strengthening the immune system of an infant or an unborn child; and/or minimizing the occurrence or severity of at least one immune system related disorder of an infant after birth, the method consisting of administering to a woman pregnant with the child, a composition comprising:
   (a) a first water soluble, non-digestible saccharide selected from the group consisting of transgalactooligosaccharides and galactooligosaccharides; and
   (b) a second water soluble, non-digestible saccharide selected from the group consisting of fructopolysaccharides, fructooligosaccharides, and inulin; and optionally
   (c) fats, proteins, digestible carbohydrates, vitamins and/or minerals.

2. The method according to claim 1, wherein the immune system related disorder is selected from the group consisting of allergy, eczema, asthma, and wheezing.

3. The method according to claim 1, wherein the first saccharide is administered in a dose of 0.5 to 50 g/day, during at least 2 weeks before due delivery.

4. The method according to claim 1, wherein bacterial colonisation of the intestine of the infant is stimulated; and/or wherein the percentage of bifidobacteria and/or lactobacilli based on total bacteria in the colon and/or faeces of the infant after birth is enhanced.

5. The method according to claim 1, wherein the second saccharide is inulin.

6. The method according to claim 1, wherein the first saccharide is galactooligosaccharide and the second saccharide is inulin.

* * * * *